United States Patent [19]
Rivers

[11] Patent Number: 5,152,927
[45] Date of Patent: Oct. 6, 1992

[54] WATER CLARIFIER

[75] Inventor: Gordon T. Rivers, Tulsa, Okla.

[73] Assignee: Chemlink, Inc., Plano, Tex.

[21] Appl. No.: 474,199

[22] Filed: Jan. 31, 1990

[51] Int. Cl.$^5$ .............. B01D 17/04; B01D 17/05; C07C 333/16
[52] U.S. Cl. .................. 252/344; 252/358; 210/708; 558/239; 562/27
[58] Field of Search .......... 252/344, 358; 558/237, 558/239, 49, 50; 210/708; 208/188; 562/27

[56] References Cited

U.S. PATENT DOCUMENTS

| | | | |
|---|---|---|---|
| 4,689,177 | 8/1987 | Thompson et al. | 252/344 |
| 4,826,625 | 5/1989 | Thompson et al. | 252/344 |
| 4,864,075 | 9/1989 | Thompson et al. | 558/237 |
| 5,006,274 | 4/1991 | Durham et al. | 210/708 X |
| 5,013,451 | 5/1991 | Thompson et al. | 210/708 |
| 5,026,483 | 6/1991 | Thompson et al. | 210/708 |

*Primary Examiner*—Robert L. Stoll
*Assistant Examiner*—Daniel S. Metzmaier
*Attorney, Agent, or Firm*—Rosenblatt & Associates

[57] ABSTRACT

A Mannich reaction of a polyfunctional amine followed by dithiocarbamate formation produces a composition useful as a water clarifier.

11 Claims, 1 Drawing Sheet where x + y + z = 5.3 (approximately)

where x + y + z = 5.3 (approximately)

WATER CLARIFIER

BACKGROUND OF THE INVENTION

1. Field of the Invention

This invention relates to highly polar organic amino derivatives useful in coagulating low-internal-phase oil-in-water emulsions of petroleum or petroleum products.

2. Prior Art

There are a large number of materials useful ranging from simple inorganic salts to complex organic compounds—U.S. Pat. Nos. 4,689,177, 4,826,625 and 4,864,075 disclose tridithiocarbamic acid compounds as having utility in this area.

SUMMARY OF THE INVENTION

A commercially available triamine, sold as Jeffamine ® T-403 by Jefferson Chemical, has the following structure

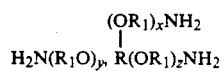

$$\begin{array}{c} (OR_1)_xNH_2 \\ | \\ H_2N(R_1O)_y R(OR_1)_zNH_2 \end{array}$$

R represents a lower alkylene group
$R_1$ represents a lower alkylene group
x, y, and z represent integers which may e the same or different, but each must at least equal 1, and the sum of x, y and z is from 3 to about 250.

Lower alkylene groups include branched and unbranched alkylene groups of from 1 to 30 carbon atoms, e.g., methylene and its homologues up to triacontylene. The generic name applied herein to compounds of this type is polyoxypropylene triamine, (POPT herein).

Certain derivatives of POPT have been found to have unexpectedly great utility, in particular one having the following representative structure:

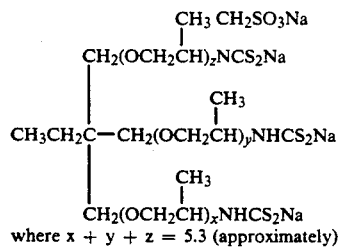

$$\begin{array}{c} CH_3 \quad CH_2SO_3Na \\ | \\ CH_2(OCH_2CH)_zNCS_2Na \\ | \\ CH_3 \\ | \\ CH_3CH_2C-CH_2(OCH_2CH)_yNHCS_2Na \\ | \\ CH_3 \\ | \\ CH_2(OCH_2CH)_xNHCS_2Na \end{array}$$

where x + y + z = 5.3 (approximately)

Figure 1:
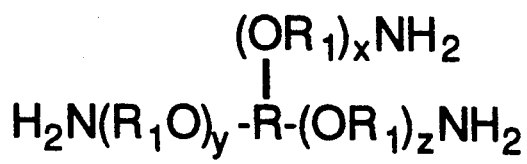
FIG. 1 is the structure of a commercially available triamine, sold as "Jeffamine ® T-403" by Jefferson Chemical.
Figure 2:
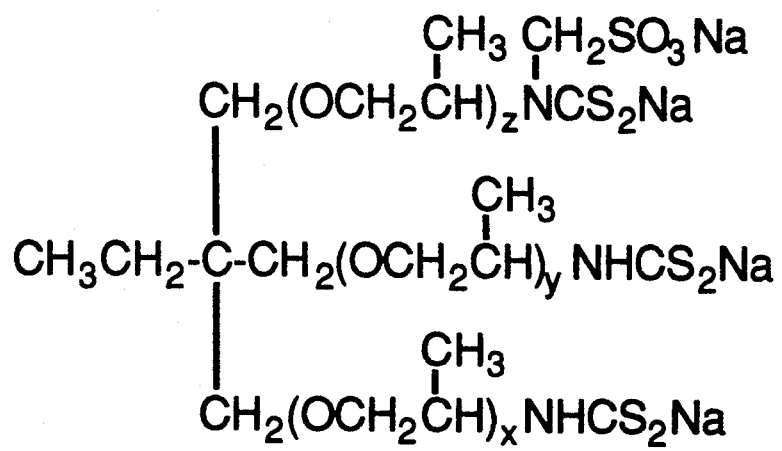
FIG. 2 is the inventive structure.

The compound in FIG. 2 is produced by the Mannich reaction of amine with formaldehyde and bisulfite followed by dithiocarbamate formation with amine, carbon disulfide and sodium hydroxide.

The compound above is prepared as follows:
Water: 34.87%
$NaHSO_3$: 6.17%
$CH_2O$ 37%: 4.80%
POPT: 26.33%
NaOH 50%: 15.66%
$CS_2$: 12.17%.

The reagents are added in the order listed, with agitation, cooling the reactor during the $CS_2$ addition.

The oil-in-water dispersions separable by the compounds of the invention are generally crude petroleum or petroleum products with a low concentration of the dispersed phase in fresh or salt water. They may be formed during petroleum production, refining, and at many other points in the production of petrochemicals and use of petroleum products.

These dispersions may have as emulsifiers certain natural compounds or none at all, and in that instance are formed by mechanical forces only, depending on the many factors involved, e.g. viscosity, salt content of water, agitation, or temperature. Most often the dispersed phase is present at only a few percent of the total. Some of these dispersions are surprisingly difficult to break, and much effort has been expended to develop demulsifiers, with varying success.

DETAILED DESCRIPTION OF THE INVENTION

This composition is effective upstream of precipitators, gas flotation, and skim tanks. Injection rates vary from 5 ppm to 25 ppm continuously depending on severity of oil carryover. Oil removed from produced water is 90%–95% effective. Example: Oil content in water before the use of this composition was averaging 150–160 ppm. After injection of this composition was initiated, oil content stabilized to 15 ppm. It does not tend to gunk compared to competitive products.

EXAMPLE 1

Bottle Test Results

In a 150 ml test bottle was placed a 100 ml sample of oil field brine containing an oil in water dispersion from an off-shore oil lease. The sample was treated with 20 ppm of my composition and shaken by hand 50 to 100 times. A black floc separated from the test sample producing bright and clear water.

EXAMPLE 2

Tabulated below are the results of other bottle tests with brines from various areas.

| Site | Dose | Result |
| --- | --- | --- |
| New Orleans | 10 ppm | bright clear water |
| New Orleans | 20 to 30 ppm | bright clear water |
| Amelia | 20 ppm | bright clear water |
| Bayou Salle | 100 ppm | bright clear water |
| Grand Lake | 30 to 40 ppm | bright clear water |
| Vermillion | 75 to 100 ppm | bright clear water |
| Eugene Island | 60 to 100 ppm | bright clear water |

What is claimed is:

1. A composition of matter useful as a demulsifier for oil-in-water emulsions comprising a compound represented by the formula:

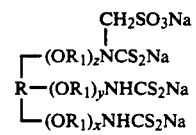

$$R \begin{cases} (OR_1)_zNCS_2Na \\ (OR_1)_yNHCS_2Na \\ (OR_1)_xNHCS_2Na \end{cases} \quad \text{with } CH_2SO_3Na$$

wherein R and $R_1$ each independently represent branched or unbranched alkylene groups of 1 to 30 carbon atoms and x, y and x are integers of at least one, their sum being from 3 to 250.

2. The composition of claim 1 wherein the sum of x, y and z is about 5.3.

3. A composition of matter useful as a demulsifier for oil-in-water emulsions comprising a compound represented by the formula:

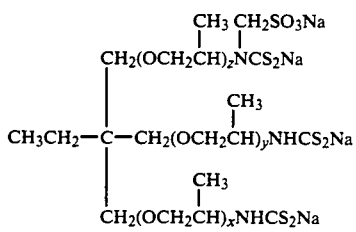

wherein x, y and z are integers of at least one, their sum being from 3 to 250.

4. The composition of claim 3 wherein the sum of x, y and z is about 5.3.

5. A method for demulsifying an oil-in-water emulsion comprising the steps of:
adding to the oil-in-water emulsion a demulsifying effective amount of a
composition of matter comprising the formula:

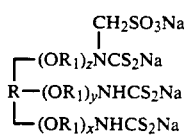

wherein R and $R_1$ each independently represent branched or unbranched alkylene groups of 1 to 30 carbon atoms and x, y and z are integers of at least one, their sum being from 3 to 250; and
recovering demuslified oil from the emulsion.

6. The method of claim 5 wherein the sum of x, y and z is about 5.3.

7. The method of claim 5 wherein R is

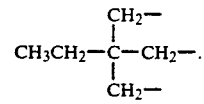

8. The method of claim 5 where every $R_1$ is

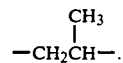

9. The method of claim 5 where the composition of matter comprises the formula:

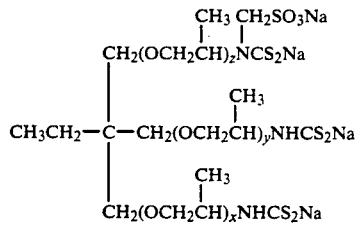

wherein x, y and z are integers of at least one, their sum being from 3 to 250.

10. The method of claim 5 where the effective amount of the composition of matter ranges from about 5 to about 100 ppm based on the oil-in-water emulsion.

11. The method of claim 5 where the effective amount of the composition of matter ranges from about 5 to about 25 ppm based on the oil-in-water emulsion.

* * * * *